(12) United States Patent
Lee et al.

(10) Patent No.: US 12,247,006 B2
(45) Date of Patent: Mar. 11, 2025

(54) PREPARING METHOD OF LINEAR CARBONATE COMPOUNDS

(71) Applicants: RESEARCH & BUSINESS FOUNDATION SUNGKYUNKWAN UNIVERSITY, Suwon-si (KR); INSTITUTE FOR BASIC SCIENCE, Daejeon (KR)

(72) Inventors: Hyoyoung Lee, Suwon-si (KR); Thi Kim Chau Nguyen, Suwon-si (KR); Jinsun Lee, Suwon-si (KR)

(73) Assignees: Research & Business Foundation Sungkyunkwan University, Suwon-si (KR); INSTITUTE FOR BASIC SCIENCE, Daejeon (KR)

( * ) Notice: Subject to any disclaimer, the term of this patent is extended or adjusted under 35 U.S.C. 154(b) by 414 days.

(21) Appl. No.: 17/534,789

(22) Filed: Nov. 24, 2021

(65) Prior Publication Data

US 2022/0169591 A1    Jun. 2, 2022

(30) Foreign Application Priority Data

Nov. 27, 2020    (KR) .................... 10-2020-0162052

(51) Int. Cl.

| | |
|---|---|
| *C07C 68/04* | (2006.01) |
| *B01J 21/06* | (2006.01) |
| *B01J 23/30* | (2006.01) |
| *B01J 23/50* | (2006.01) |
| *B01J 35/39* | (2024.01) |

(52) U.S. Cl.
CPC ............. *C07C 68/04* (2013.01); *B01J 21/063* (2013.01); *B01J 23/30* (2013.01); *B01J 23/50* (2013.01); *B01J 35/39* (2024.01)

(58) Field of Classification Search
CPC .. C07C 68/04; B01J 35/39; B01J 23/30; B01J 23/50; B01J 21/063
See application file for complete search history.

(56) References Cited

FOREIGN PATENT DOCUMENTS

KR    10-2042995 B1    11/2019

OTHER PUBLICATIONS

Fu et al. "TiO2-Doped CeO2 Nanorod Catalyst for Direct Conversion of CO2 and CH3OH to Dimethyl Carbonate: Catalytic Performance and Kinetic Study" ACS Omega, 2018, vol. 3, No. 1, pp. 198-207.*

Fronzi et al. "Reactivity of metal oxide nanocluster modified rutile and anatase TiO2: Oxygen vacancy formation and CO2 interaction" Applied Catalysis A: General, 2016, vol. 521, pp. 240-249.*

* cited by examiner

*Primary Examiner* — Matthew P Coughlin
*Assistant Examiner* — Quincy McKoy
(74) *Attorney, Agent, or Firm* — NSIP Law (57) ABSTRACT

Provided is a preparing method of linear carbonate compounds, including performing a coupling reaction of carbon dioxide in the presence of a titanium dioxide complex. The titanium dioxide complex includes an anatase phase and a rutile phase, a reduced titanium dioxide which is formed by selectively reducing any one of the anatase phase and the rutile phase, and a metallic oxide bound to the reduced titanium dioxide.

9 Claims, 10 Drawing Sheets

PREPARING METHOD OF LINEAR CARBONATE COMPOUNDS

CROSS-REFERENCE TO RELATED APPLICATIONS

This application claims the priority of Korean Patent Application No. 10-2020-0162052 filed on Nov. 27, 2020, in the Korean Intellectual Property Office, the disclosure of which is incorporated herein by reference.

BACKGROUND

Field

The present disclosure relates to a preparing method of linear carbonate compounds.

Description of the Related Art

Carbon dioxide is a major gas produced from burning and causes global warming. The concentration of carbon dioxide in the air reached unprecedented levels. As the combustion rate of fossil fuels increases, the concentration of carbon dioxide also increases continuously, which causes concern about climate change and sea level rise.

Therefore, conversion of carbon dioxide into carbon monoxide using sunlight is important in that carbon dioxide, which causes global warming, can be reduced and carbon monoxide, which is a precursor of a high value-added chemical and fuel, can be obtained.

Dimethyl carbonate (DMC) is a colorless and odorless liquid at room temperature and is non-toxic to humans. DMC is one of the environmentally friendly chemical products and has attracted a lot of attention in the industry because it can substitute for conventionally used toxic chemicals.

The direct synthesis of DMC from carbon dioxide and methanol has been reported as the most favored method due to low cost of carbon dioxide and its environmentally friendly process.

However, according to the conventional synthesis method of DMC, carbon dioxide is thermodynamically stable and dynamically inactive, and the yield is relatively low due to inactivity of a catalyst caused by the formation of water during reaction.

Currently, there are many direct synthesis methods of DMC from carbon dioxide and methanol, but a method of preparing DMC using a photocatalyst has not been reported. In the present disclosure, the synthesis of linear carbonate compounds containing DMC, which has attracted a lot of attention in the industry as an environmentally friendly material for fuel additives, polar solvents and various promising renewable energy sources, will be presented.

Korean Patent No. 10-2042995 relates to a doped titanium dioxide photocatalyst having an anatase phase and a rutile phase, and any one of the anatase phase and the rutile phase is reduced, and the other is doped with a metal. In this patent document, only a method of preparing the photocatalyst is described, but a method of preparing linear carbonate compounds using the photocatalyst is not described.

SUMMARY

An object to be achieved by the present disclosure is to provide a preparing method of linear carbonate compounds, including performing a coupling reaction of carbon dioxide using a titanium dioxide complex as a photocatalyst.

Further, another object to be achieved by the present disclosure is to provide linear carbonate compounds prepared by the preparing method of linear carbonate compounds.

Furthermore, yet another object to be achieved by the present disclosure is to provide a photocatalyst for preparing the linear carbonate compounds in the preparing method of linear carbonate compounds.

The objects of the present disclosure are not limited to the above-described objects, and there may be other objects of the present disclosure.

According to a first aspect of the present disclosure, there is provided a preparing method of linear carbonate compounds, including performing a coupling reaction of carbon dioxide in the presence of a titanium dioxide complex. The titanium dioxide complex has an anatase phase and a rutile phase, a reduced titanium dioxide which is formed by selectively reducing any one of the anatase phase and the rutile phase, and a metallic oxide bound to the reduced titanium dioxide.

According to an exemplary embodiment of the present disclosure, the titanium dioxide complex may serve as a photocatalyst so that carbon dioxide may be reduced to carbon monoxide, but may not be limited thereto.

According to an exemplary embodiment of the present disclosure, the coupling reaction of carbon dioxide may include a reaction between carbon dioxide and alcohol, but may not be limited thereto.

According to an exemplary embodiment of the present disclosure, the alcohol may include a member selected from the group consisting of methanol, ethanol, propanol, butanol, iso-propylol and combinations thereof, but may not be limited thereto.

According to an exemplary embodiment of the present disclosure, the linear carbonate compounds may include a member selected from the group consisting of dimethyl carbonate, diethyl carbonate, methyl ethyl carbonate, dipropyl carbonate, methyl propyl carbonate, ethyl propyl carbonate, dibutyl carbonate and combinations thereof, but may not be limited thereto.

According to an exemplary embodiment of the present disclosure, the titanium dioxide complex may be doped with a metal, but may not be limited thereto.

According to an exemplary embodiment of the present disclosure, the doping may be performed by reacting the reduced titanium dioxide, a precursor of the metallic oxide and a precursor of the metal in the presence of a reducing agent, but may not be limited thereto.

According to an exemplary embodiment of the present disclosure, the metallic oxide may include a member selected from the group consisting of W, Mo, Cr, Re, Ir, Ta, Hf, Fe, Ni, Cu, Zn, Mn, Y, Zr, Sn, V, Bi, Sr, Ti, Ca, Nb, K, Na, Li and combinations thereof, but may not be limited thereto.

According to an exemplary embodiment of the present disclosure, the metal for doping may include a member selected from the group consisting of Ag, Pt, Pb, Ir, Rh, Fe, Ni, Co, Al, Mg, V, Ti, Zn, Mo, Mn, Cu, Cr, Pd and combinations thereof, but may not be limited thereto.

According to an exemplary embodiment of the present disclosure, the titanium dioxide complex may be formed by reacting the reduced titanium dioxide and a precursor of the metallic oxide, but may not be limited thereto.

According to an exemplary embodiment of the present disclosure, each of the precursor of the metallic oxide and the precursor of the metal may independently include a member selected from the group consisting of W, Ag, Mo, Cr, Re, Ir, Ta, Hf, Fe, Ni, Cu, Zn, Mn, Y, Zr, Sn, V, Bi, Sr, Ti, Ca, Nb, K, Na, Li, Pt, Pb, Rh, Co, Al, Mg, Pd and combinations thereof, but may not be limited thereto.

According to an exemplary embodiment of the present disclosure, the reducing agent may include a member selected from the group consisting of sodium borohydride ($NaBH_4$), lithium aluminum hydride ($LiAlH_4$), zinc-mercury amalgam (Zn(Hg)), oxalic acid ($C_2H_2O_4$), formic acid (HCOOH), ascorbic acid ($C_6H_8O_6$), sodium amalgam, diborane, iron(II) sulfate and combinations thereof, but may not be limited thereto.

According to a second aspect of the present disclosure, there are provided linear carbonate compounds prepared by the method according to the first aspect.

According to a third aspect of the present disclosure, there is provided a photocatalyst for preparing linear carbonate compounds, having an anatase phase and a rutile phase, a reduced titanium dioxide which is formed by selectively reducing any one of the anatase phase and the rutile phase, and a metallic oxide bound to the reduced titanium dioxide.

According to an exemplary embodiment of the present disclosure, the reduced titanium dioxide is doped with a metal, but may not be limited thereto.

The above-described aspects are provided by way of illustration only and should not be construed as liming the present disclosure. Besides the above-described exemplary embodiments, there may be additional exemplary embodiments described in the accompanying drawings and the detailed description.

According to the present disclosure, a preparing method of linear carbonate compounds includes performing a coupling reaction between carbon dioxide and alcohol in the presence of a titanium dioxide complex serving as a photocatalyst to prepare linear carbonate compounds.

Specifically, among linear carbonate compounds, dimethyl carbonate (DMC), which has attracted a lot of attention in the industry as an environmentally friendly material for fuel additives, polar solvents, and various promising renewable energy sources, can be prepared with a higher yield than that prepared by a conventional synthesis method of DMC.

Also, the titanium dioxide complex used when preparing the linear carbonate compounds has excellent band alignment and has a higher electron-hole separation efficiency due to a Z-scheme reaction, and more photoinduced electrons participate in a photocatalytic reaction.

Further, the titanium dioxide complex is doped with a metal, and the metal is highly efficient in increasing the number of reactive electrons. Therefore, it is possible to selectively convert carbon dioxide into carbon monoxide.

Furthermore, the titanium dioxide complex can serve as a photocatalyst at wavelengths even in the visible and/or infrared region unlike titanium dioxide which has conventionally been used as a photocatalyst at wavelengths only in the ultraviolet region.

Moreover, as for the titanium dioxide complex doped with the metal, the quantity adsorbed and quantity desorbed increase due to an increase in adsorption volume and pore size so that the amount of material participating in the reaction may increase.

The effects to be achieved by the present disclosure are not limited to the above-described effects, and there may be other effects of the present disclosure.

BRIEF DESCRIPTION OF THE DRAWINGS

The above and other aspects, features and other advantages of the present disclosure will be more clearly understood from the following detailed description taken in conjunction with the accompanying drawings, in which.

(A) of FIG. 3 is a transmission electron microscopy (TEM) image of a titanium dioxide complex according to an example of the present disclosure, (B) of FIG. 3 and (C) of FIG. 3 are high-angle annular dark-field scanning transmission electron microscopy (HAADF-STEM) images of the titanium dioxide complex according to an example of the present disclosure, and (D) of FIG. 3 is an energy dispersive X-ray scanning transmission electron microscopy (EDX-STEM) image of the titanium dioxide complex according to an example of the present disclosure.

DETAILED DESCRIPTION OF THE EMBODIMENT

Hereafter, exemplary embodiments will be described in detail with reference to the accompanying drawings so that the present disclosure may be readily implemented by a person with ordinary skill in the art.

However, it is to be noted that the present disclosure is not limited to the exemplary embodiments but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the terms "on", "above", "on an upper end", "below", "under", and "on a lower end" that are used to designate a position of one element with respect to another element include both a case that the one element is adjacent to the other element and a case that any other element exists between these two elements.

Through the whole document, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereafter, a preparing method of linear carbonate compounds, linear carbonate compounds prepared by the preparing method and a photocatalyst for preparing the linear carbonate compounds of the present disclosure will be described in detail with reference to embodiments, examples and the accompanying drawings. However, the present disclosure is not limited to the following embodiments, examples and drawings.

According to a first aspect of the present disclosure, there is provided a preparing method of linear carbonate compounds, including performing a coupling reaction of carbon dioxide in the presence of a titanium dioxide complex. The titanium dioxide complex has an anatase phase and a rutile phase, a reduced titanium dioxide which is formed by selectively reducing any one of the anatase phase and the rutile phase, and a metallic oxide bound to the reduced titanium dioxide.

Conversion of carbon dioxide, which causes global warming, into useful fuels and chemicals is highly significant industrially and environmentally.

In the present disclosure, carbon dioxide is reduced and useful fuels and chemicals are synthesized by the preparing method of linear carbonate compounds, including a coupling reaction of carbon dioxide.

In the present disclosure, a titanium dioxide having an anatase phase and a rutile phase is mixed with a reducing agent to reduce the titanium dioxide having the anatase phase and the rutile phase to a reduced blue titanium dioxide, and the reduced blue titanium dioxide is selectively doped with a metal and chemically bound to a metallic oxide to prepare a titanium dioxide complex. The titanium dioxide complex is used as a photocatalyst to prepare a linear carbonate compound.

Figure 1:
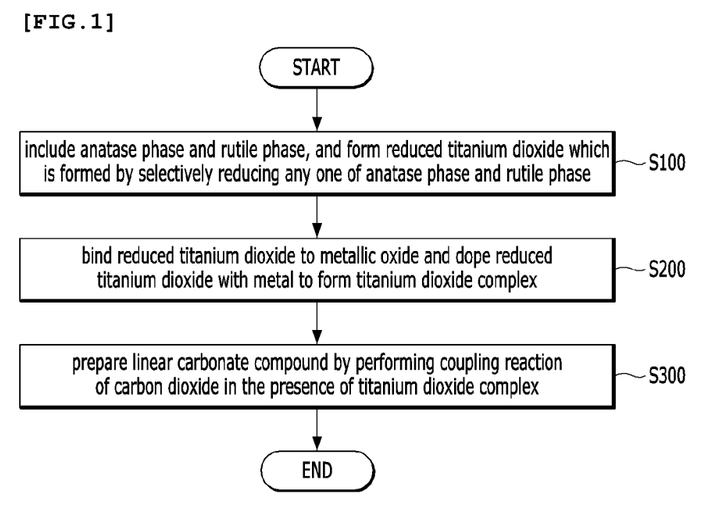
FIG. 1 is a flowchart illustrating an example processing flow for preparing a linear carbonate compound according to an exemplary embodiment of the present disclosure.

Hereafter, the preparing method of linear carbonate compounds according to the present disclosure will be described with reference to FIG. 1.

First, a reduced titanium dioxide having an anatase phase and a rutile phase, any one of which is selectively reduced, is prepared (S100).

A natural titanium dioxide exists in nature in the form of an anatase and/or rutile, and its properties may be changed depending on various factors such as the ratio of the two phases. In general, the titanium dioxide has a band gap of about 3.1 eV.

The rutile phase according to the present disclosure is also known as rutile, and most of titanium dioxide in nature has a rutile phase. The rutile phase is excellent in weatherability, hiding power, white luminance and permittivity compared with the anatase phase.

The anatase phase according to the present disclosure is excellent in photocatalytic activity for degrading pollutants present in water or air, and when a titanium dioxide having the anatase phase is coated on another material, the wear resistance may be improved.

When light is irradiated to a titanium dioxide having the rutile phase and/or the anatase phase, it can be used for various purposes such as photocatalyst, solar cell, removal of organic materials. However, if a natural titanium dioxide is used without any processing, it has a relatively low efficiency and reacts only to light of a specific wavelength and thus is not suitable for commercialization.

A reduced titanium dioxide according to the present disclosure is a material in which at least one of the rutile phase and the anatase phase is reduced and the other is not reduced. For example, the reduced titanium dioxide may have a reduced rutile phase and an unreduced anatase phase, or may have a reduced anatase phase and an unreduced rutile phase, but may not be limited thereto.

The reduced titanium dioxide is formed by mixing titanium dioxide having an anatase phase and a rutile phase with a reducing agent and selectively reducing any one of the anatase phase and the rutile phase.

The reducing agent may include alkali metals and amines, but may not be limited thereto.

The alkali metals may include a metal selected from the group consisting of Li, Na, K and combinations thereof, but may not be limited thereto.

The amines may include a liquid ammonium-based material selected from the group consisting of ethylenediamine, propylenediamine, methylenediamine, ethylamine, 1,2-dimethoxyethane, hexamethyleneimine, diisopropylamine, diethanolamine, polyethyleneimine and combinations thereof, a member selected from the group consisting of ethylenediaminetetraacetic acid, diethylenetriamine pentaacetic acid, diaminohydroxypropane tetraacetic acid and combinations thereof, or a liquid amine for forming solvated electrons, selected from the group consisting of tetrahydrofuran, dimethyl sulfoxide, hexamethylphosphoramide, diethylamine, triethylamine, diethylenetriamine, toluenediamine, m-phenylenediamine, diphenylmethane diamine, hexamethylenediamin, triethylenetetramine, tetraethylenepentamine, hexamethylenetetramine, ethanolamine, diethanolamine, triethanolamine and combinations thereof, but may not be limited thereto.

The reduction may be performed in a sealed and anhydrous state, but may not be limited thereto.

The reduction may be performed at room temperature, but may not be limited thereto.

Then, the reduced titanium dioxide may be bound to a metallic oxide and doped with a metal to prepare a titanium dioxide complex (S200).

According to an exemplary embodiment of the present disclosure, the bond of the reduced titanium dioxide with the metallic oxide may be formed by reacting the reduced titanium dioxide with a precursor of the metallic oxide, but may not be limited thereto.

The bond of the reduced titanium dioxide with the metallic oxide may be a chemical bond, but may not be limited thereto.

According to an exemplary embodiment of the present disclosure, the metallic oxide may include a member selected from the group consisting of W, Mo, Cr, Re, Ir, Ta, Hf, Fe, Ni, Cu, Zn, Mn, Y, Zr, Sn, V, Bi, Sr, Ti, Ca, Nb, K, Na, Li and combinations thereof, but may not be limited thereto.

Preferably, the metallic oxide may be a tungsten trioxide ($WO_3$), but may not be limited thereto.

According to an exemplary embodiment of the present disclosure, the titanium dioxide complex may be doped with a metal, but may not be limited thereto.

According to an exemplary embodiment of the present disclosure, the metal for doping may include a member selected from the group consisting of Ag, Pt, Pb, Ir, Rh, Fe, Ni, Co, Al, Mg, V, Ti, Zn, Mo, Mn, Cu, Cr, Pd and combinations thereof, but may not be limited thereto.

Preferably, the metal for doping may be Ag, but may not be limited thereto.

The metallic oxide bound to the reduced titanium dioxide and the metal doped on the reduced titanium dioxide may be different from each other in kind, but may not be limited thereto.

The metal for doping may supply electrons onto the reduced titanium dioxide, but may not be limited thereto.

The electrons on the metal for doping are vibrated by localized surface plasmon resonance and thus can be transferred onto the valence band of the reduced titanium dioxide or the conduction band of the metallic oxide.

The localized surface plasmon resonance according to the present disclosure refers to the phenomenon of vibration of electrons at the boundary between the surface of a metal and a dielectric material, such as the metallic oxide or the reduced titanium dioxide, when light of a predetermined wavelength is irradiated to the nanostructure surface of the metal with the size equal to or less than the predetermined wavelength.

The reduced titanium dioxide is bound to the metallic oxide or doped with the metal, and, thus, a trap site may be further formed in the band gap of the reduced titanium dioxide.

Specifically, if any one of the anatase phase and the rutile phase is reduced and the other is not reduced, the band gap between the reduced phase and the unreduced phase is broadened and a new trap site is formed in the band gap.

In addition, if the reduced titanium dioxide is bound to the metallic oxide or doped with the metal, a new trap site may be further formed in the band gap, which improves the separation efficiency of electron-hole pairs of the reduced titanium dioxide and thus lowers activation energy required for photo-excitation. Therefore, it is possible to effectively absorb light in the ultraviolet, visible and/or infrared region.

According to an exemplary embodiment of the present disclosure, the doping may be performed by reacting the reduced titanium dioxide, a precursor of the metallic oxide and a precursor of the metal in the presence of a reducing agent, but may not be limited thereto.

The titanium dioxide complex may be formed in a cooling ice tank, but may not be limited thereto.

According to an exemplary embodiment of the present disclosure, each of the precursor of the metallic oxide and the precursor of the metal may independently include a member selected from the group consisting of W, Ag, Mo, Cr, Re, Ir, Ta, Hf, Fe, Ni, Cu, Zn, Mn, Y, Zr, Sn, V, Bi, Sr, Ti, Ca, Nb, K, Na, Li, Pt, Pb, Rh, Co, Al, Mg, Pd and combinations thereof, but may not be limited thereto.

According to an exemplary embodiment of the present disclosure, the reducing agent may include a member selected from the group consisting of sodium borohydride ($NaBH_4$), lithium aluminum hydride ($LiAlH_4$), zinc-mercury amalgam (Zn(Hg)), oxalic acid ($C_2H_2O_4$), formic acid (HCOOH), ascorbic acid ($C_6H_8O_6$), sodium amalgam, diborane, iron(II) sulfate and combinations thereof, but may not be limited thereto.

Thereafter, a coupling reaction of carbon dioxide is performed in the presence of the titanium dioxide complex to prepare a linear carbonate compound (S300).

According to an exemplary embodiment of the present disclosure, the titanium dioxide complex may serve as a photocatalyst so that carbon dioxide may be reduced to carbon monoxide, but may not be limited thereto.

The titanium dioxide complex serves as a photocatalyst and selectively converts carbon dioxide into carbon monoxide.

A conventional method for converting carbon dioxide into carbon monoxide requires a noble metal catalyst and an electrolyte additive under overcurrent conditions.

However, when the titanium dioxide complex according to the present disclosure is used, it is possible to reduce the amount of emission of carbon dioxide and produce carbon monoxide, which is a precursor of a high value-added chemical and fuel, without using a noble metal catalyst.

According to an exemplary embodiment of the present disclosure, the coupling reaction of carbon dioxide may include a reaction between carbon dioxide and alcohol, but may not be limited thereto.

According to an exemplary embodiment of the present disclosure, the alcohol may include a member selected from the group consisting of methanol, ethanol, propanol, butanol, iso-propylol and combinations thereof, but may not be limited thereto.

The titanium dioxide complex according to the present disclosure induces an oxidation reaction and a reduction reaction of carbon dioxide and alcohol through the Z-scheme mechanism.

The metallic oxide and the reduced titanium dioxide may be a Z-scheme heterojunction, but may not be limited thereto.

When an electrical heterojunction is formed by different materials, it can be classified into various types depending on the sizes of the valence band and the conduction band of the two materials. For example, if the valance band of material A is greater than the valence band of material B and the conduction band of material A is smaller than the conduction band of material B, the two materials may form a straddling heterojunction (type I).

Also, if the valance band of material A is present between the valence band and the conduction band of material B and the conduction band of material A is greater than the conduction band of material B, the two materials may form a staggered heterojunction (type II).

The titanium dioxide complex in the form of a staggered heterojunction is present on the conduction band of the reduced titanium dioxide, and electrons excited by light may be transferred to the conduction band of the metallic oxide and holes present on the valence band of the metallic oxide may be transferred to the valence band of the reduced titanium dioxide.

However, the titanium dioxide complex according to the present disclosure is in the form of a Z-scheme heterojunction, and, thus, electrons excited by light to the conduction band of the metallic oxide may be transferred to the valence band of the reduced titanium dioxide. The electrons transferred to the valence band of the reduced titanium dioxide may be excited again by light to the conduction band of the reduced titanium dioxide, and electrons excited to the conduction band of the titanium dioxide may be transferred to the metal for doping and thus may selectively reduce carbon dioxide into carbon monoxide or may generate oxygen. Also, holes formed on the valence band of the metallic oxide oxidize alcohol to form radicals.

The titanium dioxide complex may be used in a process for obtaining carbon monoxide, methane ($CH_4$) and hydrogen by reducing a material, a process for removing organic materials and volatile organic compounds contained in cigarette smoke, and the like.

According to an exemplary embodiment of the present disclosure, the linear carbonate compounds may include a member selected from the group consisting of dimethyl carbonate, diethyl carbonate, ethyl methyl carbonate, dipropyl carbonate, methyl propyl carbonate, ethyl propyl carbonate, dibutyl carbonate and combinations thereof, but may not be limited thereto.

According to the preparing method of linear carbonates of the present disclosure, dimethyl carbonate (DMC), which has recently attracted a lot of attention as one of the environmentally friendly chemical products, can be synthesized with a higher yield than that synthesized by the conventional method.

DMC is a is a colorless and odorless liquid at room temperature and is non-toxic to humans. Also, DMC is an industrially important compound because it can substitute for conventionally used toxic chemicals.

According to a second aspect of the present disclosure, there are provided linear carbonate compounds prepared by the method according to the first aspect.

Detailed descriptions of the linear carbonate compounds according to the second aspect of the present disclosure, which overlap with those of the first aspect of the present disclosure, are omitted hereinafter, but the descriptions of the first aspect of the present disclosure may be identically applied to the second aspect of the present disclosure, even though they are omitted hereinafter.

According to a third aspect of the present disclosure, there is provided a photocatalyst for preparing linear carbonate compounds, having an anatase phase and a rutile phase, a reduced titanium dioxide which is formed by selectively reducing any one of the anatase phase and the rutile phase, a metallic oxide bound to the reduced titanium dioxide, and a metal doped on the reduced titanium dioxide.

According to an exemplary embodiment of the present disclosure, the reduced titanium dioxide may be doped with a metal, but may not be limited thereto.

A photocatalyst is a material that causes a catalytic reaction upon receiving light. When the photocatalyst receives light, strong oxidizing power such as ozone is generated and serves to convert and degrade an organic chemical into water and a carbon acid gas which are non-toxic and odorless.

The photocatalyst degrades a chemical in water or air and converts it into unharmful and odorless materials. The photocatalyst serves to degrade pollutants and enables self-purification. Since the photocatalyst has a high degradation ability for pollutants, it has widely been used in various fields including environment.

Detailed descriptions of the photocatalyst for preparing linear carbonate compounds according to the third aspect of the present disclosure, which overlap with those of the first aspect and/or the second aspect of the present disclosure, are omitted hereinafter, but the descriptions of the first aspect and/or the second aspect of the present disclosure may be identically applied to the third aspect of the present disclosure, even though they are omitted hereinafter.

Hereafter, the present disclosure will be described in more detail with reference to examples. The following examples are provided only for explanation, but do not intend to limit the scope of the present disclosure.

Example 1-1: Preparation of Reduced Titanium Dioxide

Hereafter, for the convenience in description, a reduced titanium dioxide in which any one of an anatase phase and a rutile phase is reduced will be denoted as BTO, and a bond of material A and material B will be denoted as A-B. For example, a titanium dioxide complex bound to a metallic oxide $WO_3$ and doped with a metal Ag as prepared by the method of the present disclosure will be denoted as Ag·W-BTO. Also, Ag·W-BTO with BTO content of 25 mg will be denoted as Ag·W-BTO(25).

The BTO photocatalyst was prepared according to a known process.

Specifically, in a titanium dioxide having an anatase phase and a rutile phase, when only the rutile phase was reduced, 14 mg of metallic Li particles was dissolved in 20 ml of ethylenediamine to form a 1 mmol/ml solvated electron solution.

200 mg of dried $TiO_2$ nanoparticles (analysis, size: 25 nm or less, rutile, size: 140 nm or less, P-25, size: 20 nm to 40 nm) was added into the solution and stirred for 7 days. The reaction was performed in a sealed and anhydrous state.

Then, a 1 mol/L HCl was slowly added into the mixture to quench the excess electrons and form Li salts.

Finally, the produced composite was rinsed by deionized water several times and dried at room temperature in a vacuum oven to obtain the BTO.

When only the anatase phase was reduced, 14 mg of metallic Na particles was dissolved in 20 ml of ethylenediamine to form a 1 mmol/ml solvated electron solution. The subsequent processes are the same as those performed when only the rutile phase is reduced.

Example 1-2: Preparation of Titanium Dioxide Complex

Figure 2:
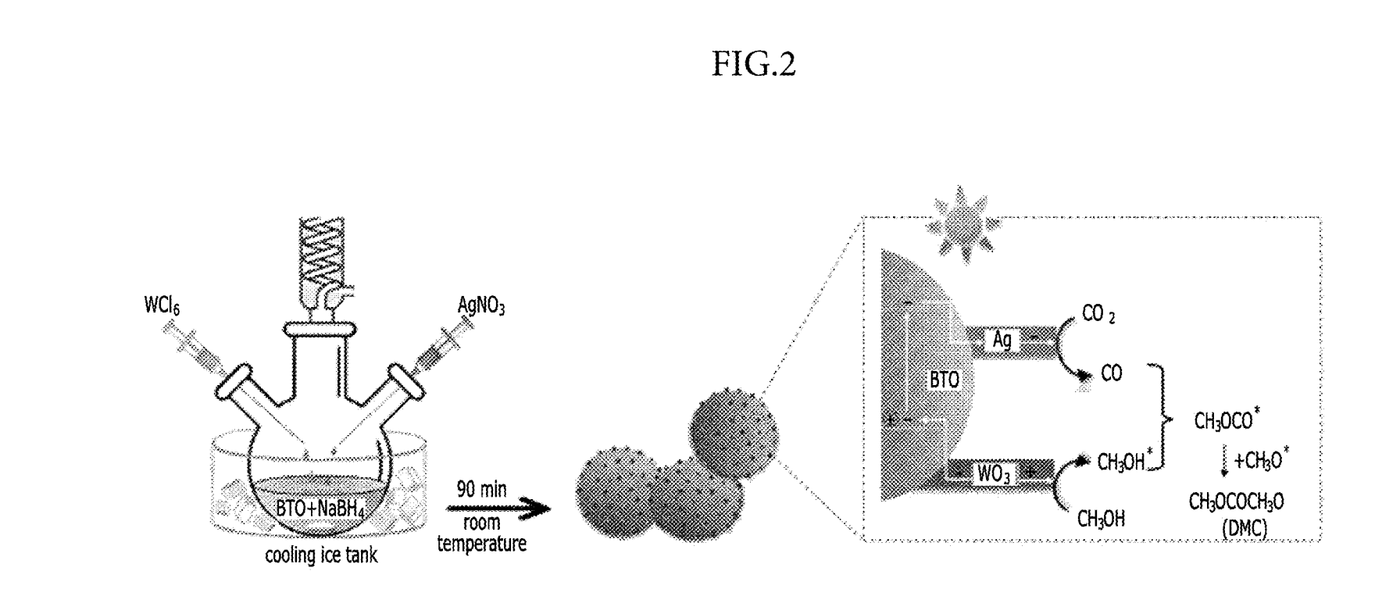
FIG. 2 is an example depiction showing a process for preparing a titanium dioxide complex and a process for synthesizing dimethyl carbonate in the presence of the titanium dioxide complex according to an example of the present disclosure.

FIG. 2 is an example depiction showing a process for preparing a titanium dioxide complex and a process for preparing dimethyl carbonate in the presence of the titanium dioxide complex according to an example of the present disclosure.

Referring to FIG. 2, in a cooling ice tank, 50 mg of sodium borohydride ($NaBH_4$), which is a strong base, was added to 25 mg of the reduced titanium dioxide prepared in Example 1 and stirred for 15 minutes under sealed and anhydrous conditions.

Then, 50 mg of silver nitrate ($AgNO_3$) as a metal precursor and 50 mg of tungsten hexachloride ($WCl_6$) as a metallic oxide precursor were added thereto at room temperature and reacted for further 90 minutes.

Through the reaction, silver (Ag) was selectively doped on the surface of the reduced titanium dioxide and the reduced titanium dioxide and a tungsten trioxide ($WO_3$) were chemically bound to form a heterojunction. As a result, a titanium dioxide complex (Ag·W-BTO(25)) was prepared.

Figure 3:
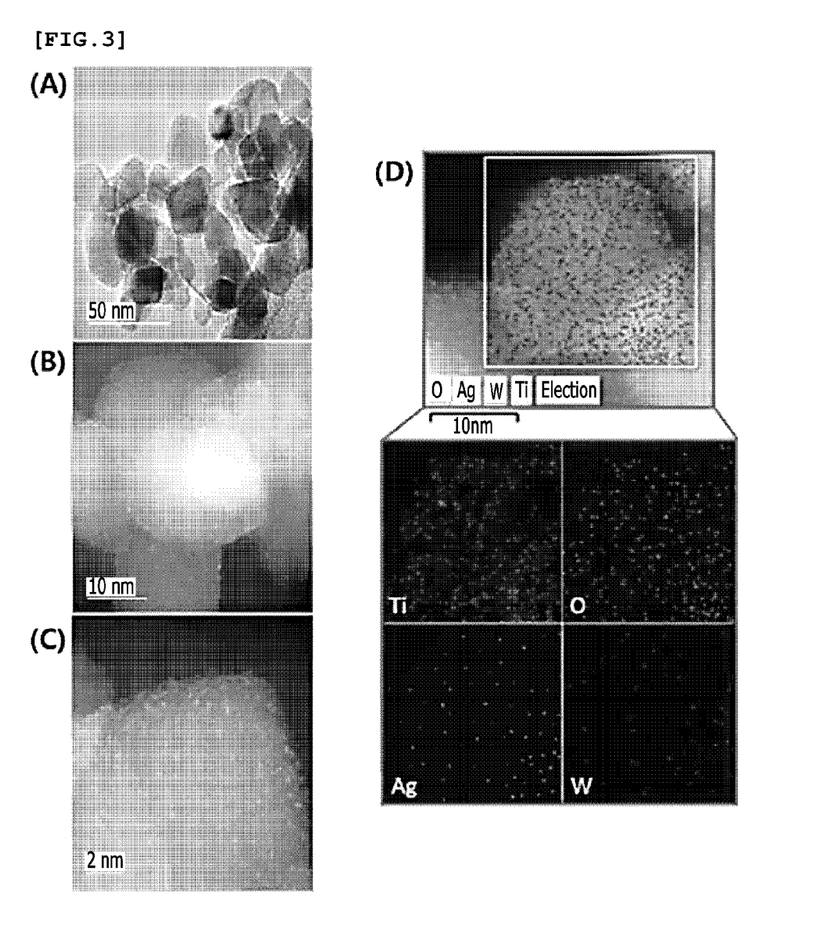

(A) of FIG. 3 is a transmission electron microscopy (TEM) image of a titanium dioxide complex according to an example of the present disclosure, (B) of FIG. 3 and (C) of FIG. 3 are high-angle annular dark-field scanning transmission electron microscopy (HAADF-STEM) images of the titanium dioxide complex according to an example of the present disclosure, and (D) of FIG. 3 is an energy dispersive X-ray scanning transmission electron microscopy (EDX-STEM) image of the titanium dioxide complex according to an example of the present disclosure.

Referring to (A) of FIG. 3 through (C) of FIG. 3, it can be seen that uniform Ag·W-BTO composed of reduced titanium dioxide nanoparticles with a diameter of 10 nm to 20 nm was obtained. Also, it can be seen that Ag and $WO_3$ nanoclusters similar in size of from about 0.2 nm to about 1 nm were loaded on the surface of the reduced titanium dioxide.

Referring to (D) of FIG. 3, the distribution of Ti, W, Ag and O were checked by performing elementary mapping through energy dispersive X-ray scanning transmission electron microscopy (EDX-STEM) on the Ag·W-BTO(25) catalyst. Apparent impurities were not detected.

Example 2: Preparation of Dimethyl Carbonate

Dimethyl carbonate was prepared through a coupling reaction of carbon dioxide and methanol by irradiating light to the titanium dioxide complex (Ag·W-BTO(25)) prepared in Example 1-2.

Referring to FIG. 2, when light is irradiated to the titanium dioxide complex, electrons and holes are formed on the conduction band and the valence band. The formed electrons are transferred from the titanium dioxide complex to the metal Ag for doping and react with carbon dioxide to selectively generate carbon monoxide (CO). The formed holes oxidize methanol in the metallic oxide ($WO_3$) bound to the titanium dioxide complex to generate a $CH_3O$ radical which is an intermediate.

The generated CO and $CH_3O$ radical are bound to form a $CH_3OCO$ radical, and another $CH_3O$ radical is sequentially bound to the $CH_3OCO$ radical to form $CH_3OCOCH_3O$ (dimethyl carbonate, DMC).

The synthesis of DMC through the reaction achieves a higher yield than the conventional synthesis method of DMC.

Comparative Example

Various photocatalysts were used as comparative examples for comparison with the titanium dioxide complex of the present disclosure in characteristics and performance.

Specifically, a reduced titanium dioxide (BTO) which has an anatase phase and a rutile phase and in which any one of the anatase phase and the rutile phase is selectively reduced, a titanium dioxide complex (W-BTO) in which the reduced titanium dioxide is bound to $WO_3$, and a titanium dioxide complex (Ag-BTO) in which the reduced titanium dioxide is bound to Ag were compared with the titanium dioxide complex of the present disclosure.

Test Example 1

Figure 4:
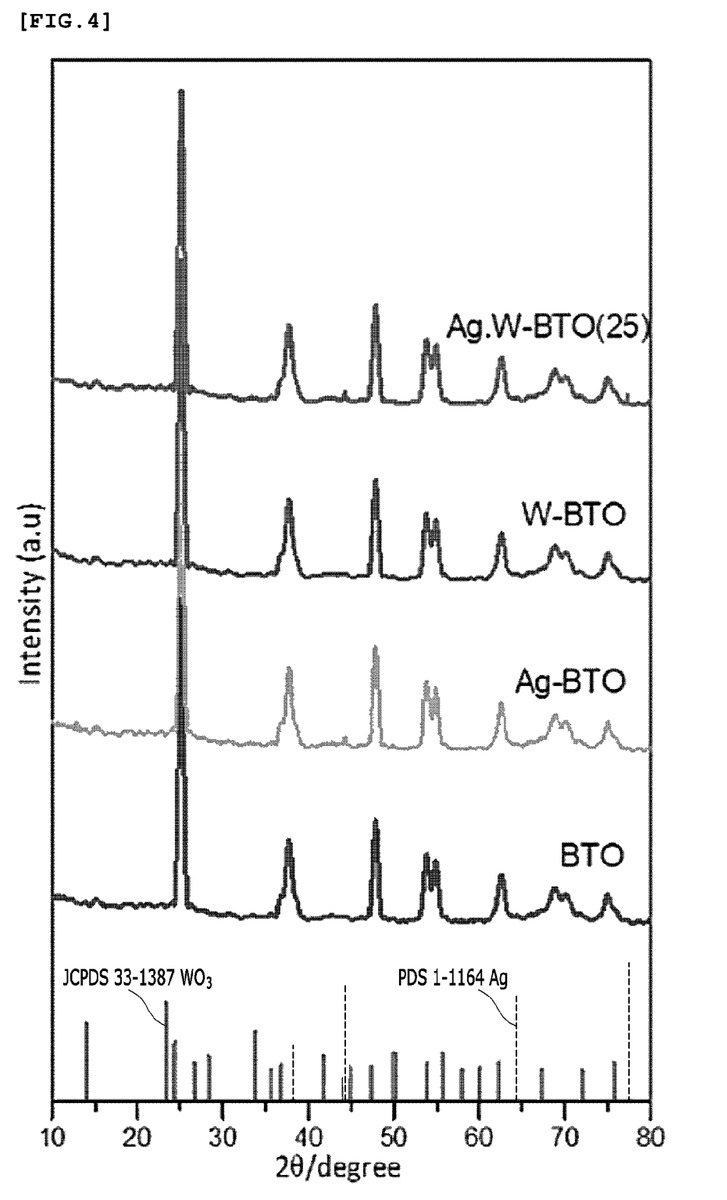
FIG. 4 shows XRD patterns of various photocatalysts according to an example and a comparative example of the present disclosure.

FIG. 4 shows XRD patterns of Ag·W-BTO(25), W-BTO, Ag-BTO and BTO catalysts according to an example and a comparative example of the present disclosure.

Referring to FIG. 4, the crystal structure of Ag nanoparticles on the Ag-BTO and Ag·W-BTO(25) was observed to be metallic silver Ag (JCPDS 1-1164).

BTO nanoparticles were found to have an XRD spectrum with only the representative peaks of the anatase phase.

The peaks of the rutile phase disappeared after the titanium dioxide was treated with a reducing agent so that the band gap was narrowed, and light absorption was improved. Also, both the W-BTO and Ag·W-BTO(25) spectra showed additional peaks assigned to the (202) plane of monoclinic $WO_3$.

Test Example 2

Figure 5:
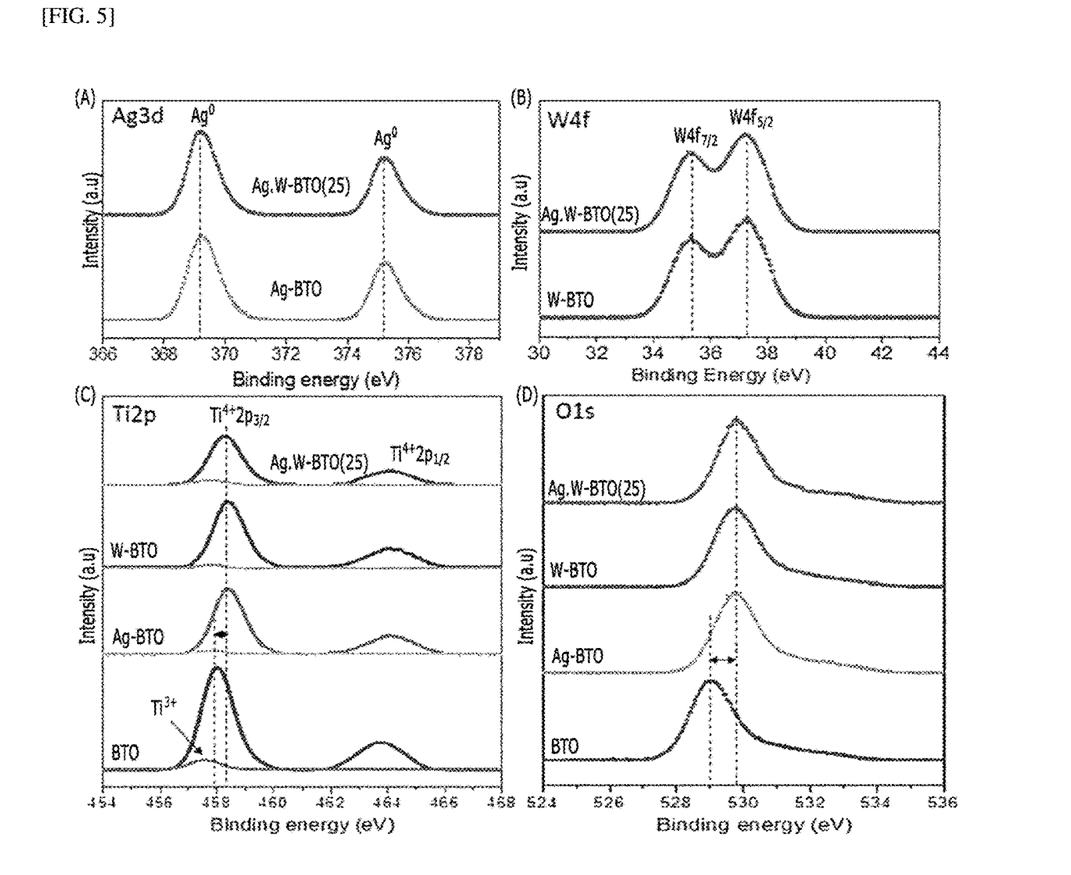
FIG. 5 shows XPS spectra of various photocatalysts according to the example and the comparative example of the present disclosure.

FIG. 5 shows XPS spectra of Ag·W-BTO(25), W-BTO, Ag-BTO and BTO catalysts according to the example and the comparative example of the present disclosure.

Referring to (A) of FIG. 5 and (B) of FIG. 5, it can be seen from comparison between the XPS spectra of Ag 3d and W 4f that the binding energy of Ag 3d and W 4f did not change before and after loading of Ag·W-BTO(25).

Also, $Ag^0$ appeared in both Ag-BTO and Ag·W-BTO(25).

Further, the formation of $WO_3$ was confirmed by $W\ 4f_{7/2}$ and $W\ 4f_{5/2}$ in W-BTO and Ag·W-BTO(25).

Referring to (C) of FIG. 5, it can be seen from the Ti 2p XPS of the reduced titanium dioxide that after the reduced titanium dioxide was doped with a metal and bound to a metallic oxide, electrons of the metal were distributed in Ti3+ so that the peak shifted to a higher binding energy.

Two broad peaks were observed at 457.97 eV and 463.89 eV respectively corresponding to $Ti^{4+}\ 2p_{3/2}$ and $Ti^{4+}\ 2p_{1/2}$, which are characteristics of $Ti^{4+}$ peaks.

A smaller peak at 457.65 eV, which is a characteristic of $Ti^+$, indicates that $Ti^+$ was generated on the surface of the reduced titanium dioxide. However, the intensity of $Ti^{3+}$ decreased after Ag and/or $WO_3$ was added to the reduced titanium dioxide, which means that the titanium dioxide formed a bond with W and/or Ag.

Referring to (D) of FIG. 5, after the metal and/or the metallic oxide was bound to the reduced titanium dioxide, the peak shifted to a higher binding energy in the O 1s core-level XPS spectra, which was further demonstrated by the presence of an O—Ti bond, an O—W bond and an OH group in Ag·W-BTO.

Test Example 3

Figure 6:
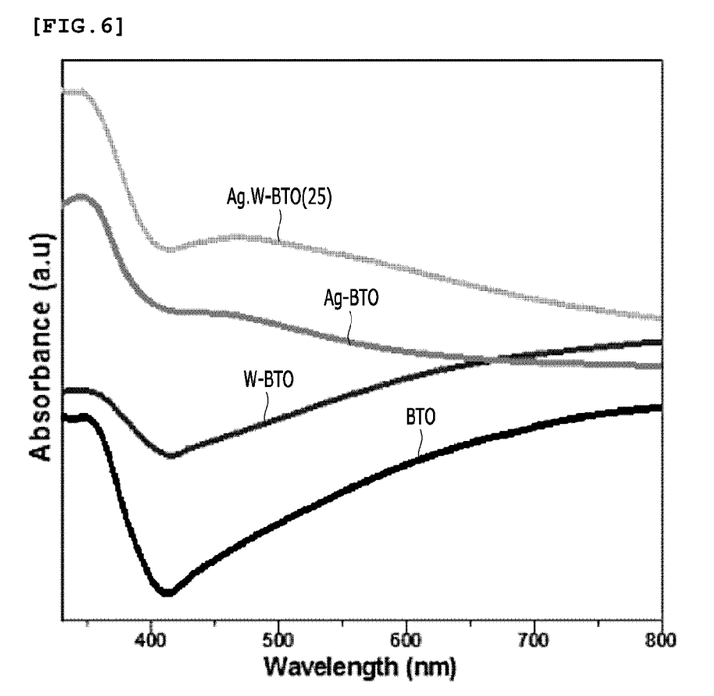
FIG. 6 shows UV-vis spectra of various photocatalysts according to the example and the comparative example of the present disclosure.

FIG. 6 shows UV-vis spectra of Ag·W-BTO(25), W-BTO, Ag-BTO and BTO catalysts according to the example and the comparative example of the present disclosure.

Referring to FIG. 6, it can be seen that BTO showed absorption at a wavelength of 420 nm or more, W-BTO showed a slight improvement in light absorption compared with BTO.

However, it can be seen that the presence of Ag on Ag-BTO and Ag·W-BTO(25) showed strong absorption expansion and light absorption in a broad range of wavelength of from 300 nm to 800 nm. It is assumed that this may result from the localized surface plasmon resonance (LSPR) effect of metallic Ag atoms on the surfaces of BTO and $WO_3$.

Test Example 4

The separation and recombination of photoexcited charge carriers on Ag·W-BTO(25) were examined by comparing the PL spectra.

Figure 7:
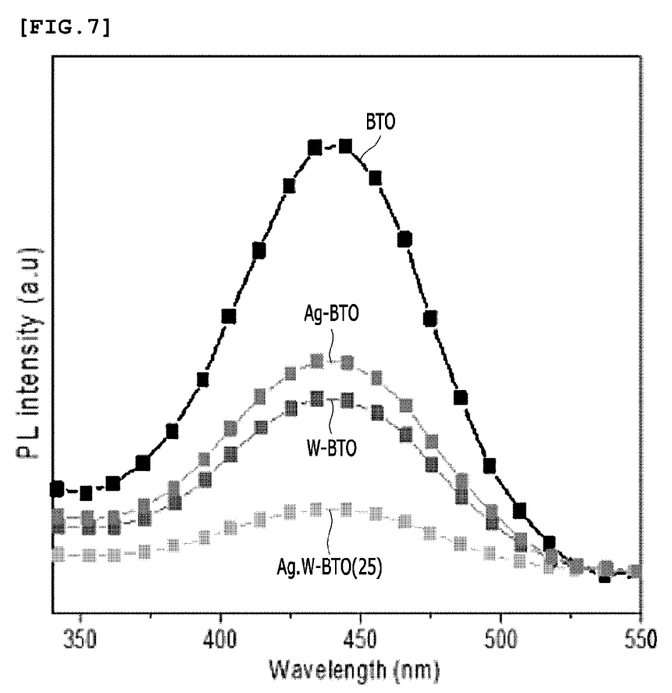
FIG. 7 shows PL spectra of various photocatalysts according to the example and the comparative example of the present disclosure.

FIG. 7 shows PL spectra of Ag·W-BTO(25), W-BTO, Ag-BTO and BTO photocatalysts according to the example and the comparative example of the present disclosure.

Referring to FIG. 7, BTO showed the PL spectrum with the highest PL intensity due to the recombination of photoexcited electrons and holes.

In contrast, Ag·W-BTO(25) showed the PL spectrum with a lower PL intensity than W-BTO and Ag-BTO, which shows a higher electron-hole separation efficiency due to the Z-scheme mechanism that enables more photoexcited electrons to participate in a photocatalytic reaction.

Test Example 5

Figure 8:
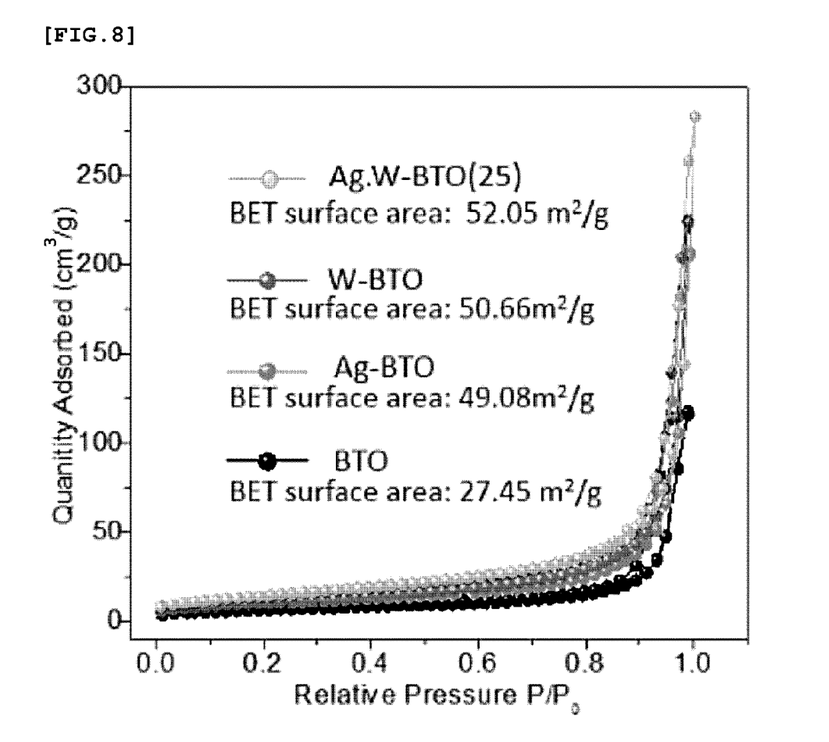
FIG. 8 is a graph showing nitrogen adsorption-desorption of various photocatalysts according to the example and the comparative example of the present disclosure.

FIG. 8 is a graph showing nitrogen adsorption-desorption of Ag·W-BTO(25), W-BTO, Ag-BTO and BTO photocatalysts according to the example and the comparative example of the present disclosure.

Referring to FIG. 8, all the photocatalysts showed a remarkable hysteresis loop at a high relative pressure (P/P0>0.4).

Among the four samples, Ag·W-BTO(25) exhibited the highest quantity adsorbed and the greatest BET surface area and BTO exhibited the lowest quantity adsorbed and the smallest BET surface area, which confirmed that loading of Ag and $WO_3$ nanoclusters caused an improvement in surface area and gas trapping ability during a photocatalytic reaction.

Test Example 6

Figure 9:
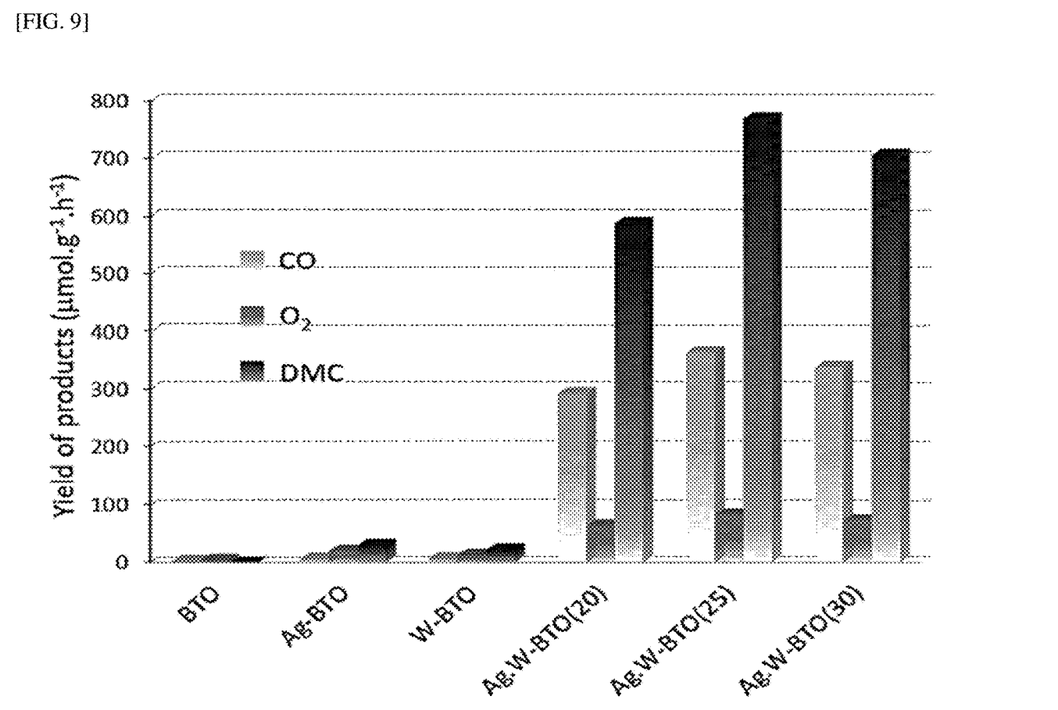
FIG. 9 is a graph showing the yields of carbon monoxide (CO), oxygen ($O_2$) and dimethyl carbonate (DMC) in the presence of various photocatalysts according to an example and a comparative example of the present disclosure.

FIG. 9 is a graph showing the yields of carbon monoxide (CO), oxygen ($O_2$) and dimethyl carbonate (DMC) in the presence of BTO, Ag-BTO, W-BTO, Ag·W-BTO(20), Ag·W-BTO(25) and Ag·W-BTO(30) photocatalysts according to an example and a comparative example of the present disclosure.

The numbers in brackets of Ag·W-BTO(20), Ag·W-BTO(25) and Ag·W-BTO(30) refer to the amounts (mg) of BTO.

Referring to FIG. 9, the yields of CO, $O_2$ and DMC with various photocatalysts under sunlight irradiation for 12 hours were checked.

When BTO was used as a photocatalyst, the production of DMC was not observed, and when Ag-BTO and W-BTO were used as a photocatalyst, the yields of products were low due to lack of active sites for reduction and oxidation.

Also, the optimized catalyst Ag·W-BTO(25) exhibited the highest yield of DMC of 788 mmol $g^{-1}$ $h^{-1}$ compared with Ag·W-BTO(20) and Ag·W-BTO(30).

Test Example 7

Figure 10:
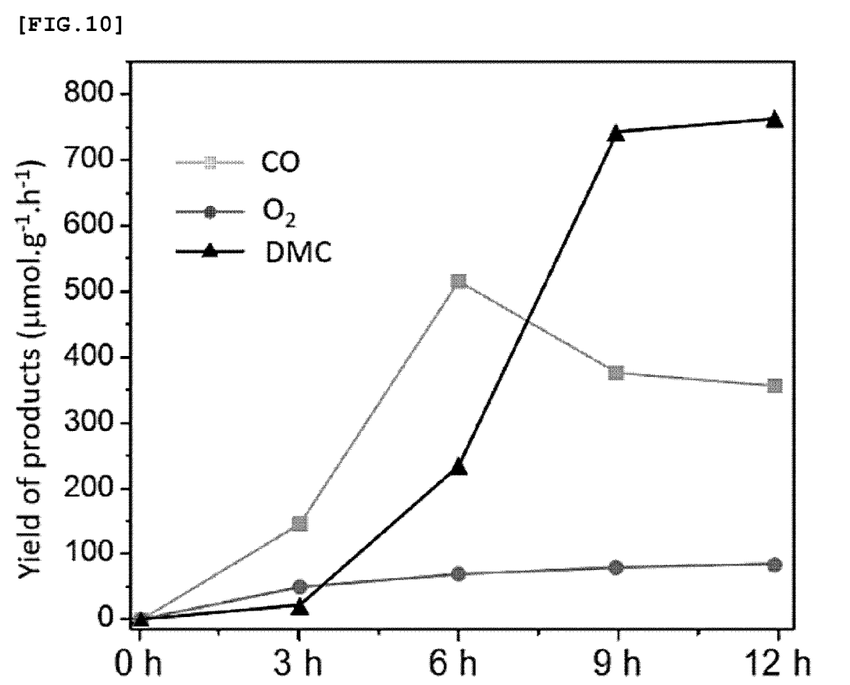
FIG. 10 is a graph showing the yields of carbon monoxide (CO), oxygen ($O_2$) and dimethyl carbonate (DMC) in the presence of the titanium dioxide complex according to an example of the present disclosure.

FIG. 10 is a graph showing the yields of carbon monoxide (CO), oxygen ($O_2$) and dimethyl carbonate (DMC) in the presence of Ag·W-BTO(25) photocatalyst according to an example of the present disclosure.

Referring to FIG. 10, sunlight was irradiated to the Ag. W-BTO(25) catalyst, and for 12 hours after irradiation, the yields of CO, $O_2$ and DMC were checked every 3 hours.

It can be seen that the highest yield of CO (546 mol $g^{-1}$ $h^{-1}$) was achieved at 6 h after commencement of irradiation, and the yield of CO decreased (388 mol $g^{-1}$ $h^{-1}$) in a period of from 6 h to 9 h and slightly decreased in a period of from 9 h to 12 h.

The yield of DMC greatly increased in a period of from 6 h to 9 h after commencement of irradiation. This period may be an optimal time to synthesize CO and $CH_3O$ into DMC. Accordingly, it can be seen that a decrease in the yield of CO at 6 h after commencement of irradiation was caused by the synthesis of DMC.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and exemplary embodiments conceived from the meaning and scope of the claims and their equivalents are included in the scope of the present disclosure.

What is claimed is:

1. A preparing method of linear carbonate compounds, comprising:
   performing a coupling reaction of carbon dioxide in the presence of a titanium dioxide complex,
   wherein the titanium dioxide complex has an anatase phase and a rutile phase, a reduced titanium dioxide which is formed by selectively reducing any one of the anatase phase and the rutile phase, and a metallic oxide bound to the reduced titanium dioxide,
   wherein the titanium dioxide complex is doped with a metal,
   wherein the titanium dioxide complex serves as a photocatalyst so that carbon dioxide is reduced to carbon monoxide, and
   wherein the metallic oxide includes a member selected from the group consisting of W, Mo, Cr, Re, Ir, Ta, Hf, Fe, Ni, Cu, Zn, Mn, Y, V, Bi, Sr, Ca, Nb, K, Na, Li, and combinations thereof.

2. The preparing method of linear carbonate compounds according to claim 1, wherein the coupling reaction of carbon dioxide includes a reaction between carbon dioxide and alcohol.

3. The preparing method of linear carbonate compounds according to claim 2, wherein the alcohol includes a member selected from the group consisting of methanol, ethanol, propanol, butanol, iso-propylol and combinations thereof.

4. The preparing method of linear carbonate compounds according to claim 1, wherein the linear carbonate compounds include a member selected from the group consisting of dimethyl carbonate, diethyl carbonate, methyl ethyl carbonate, dipropyl carbonate, methyl propyl carbonate, ethyl propyl carbonate, dibutyl carbonate and combinations thereof.

5. The preparing method of linear carbonate compounds according to claim 1, wherein the doping is performed by reacting the reduced titanium dioxide, a precursor of the metallic oxide and a precursor of the metal in the presence of a reducing agent.

6. The preparing method of linear carbonate compounds according to claim 1, wherein the metal for doping includes a member selected from the group consisting of Ag, Pt, Pb, Ir, Rh, Fe, Ni, Co, Al, Mg, V, Ti, Zn, Mo, Mn, Cu, Cr, Pd and combinations thereof.

7. The preparing method of linear carbonate compounds according to claim 1, wherein the titanium dioxide complex is formed by reacting the reduced titanium dioxide and a precursor of the metallic oxide.

8. The preparing method of linear carbonate compounds according to claim 5, wherein the reducing agent includes a member selected from the group consisting of sodium borohydride ($NaBH_4$), lithium aluminum hydride ($LiAlH_4$), zinc-mercury amalgam (Zn (Hg)), oxalic acid ($C_2H_2O_4$), formic acid (HCOOH), ascorbic acid ($C_6H_8O_6$), sodium amalgam, diborane, iron (II) sulfate and combinations thereof.

9. A photocatalyst for preparing linear carbonate compounds, comprising:
   an anatase phase and a rutile phase, a reduced titanium dioxide which is formed by selectively reducing any one of the anatase phase and the rutile phase, and a metallic oxide bound to the reduced titanium dioxide,
   wherein the reduced titanium dioxide complex is doped with a metal,
   wherein the reduced titanium dioxide complex serves as a photocatalyst so that carbon dioxide is reduced to carbon monoxide, and
   wherein the metallic oxide includes a member selected from the group consisting of W, Mo, Cr, Re, Ir, Ta, Hf, Fe, Ni, Cu, Zn, Mn, Y, V, Bi, Sr, Ca, Nb, K, Na, Li, and combinations thereof.

* * * * *